(12) United States Patent
Tanaka et al.

(10) Patent No.: US 6,217,991 B1
(45) Date of Patent: *Apr. 17, 2001

(54) THERMOPLASTIC RESIN-COATED METAL PLATE, AND METHOD OF AND APPARATUS FOR MANUFACTURING THE SAME

(75) Inventors: Atsuo Tanaka; Yoshiki Sakamoto; Noriaki Kaguma, all of Yamaguchi-ken (JP)

(73) Assignee: Toyo Kohan Co., Ltd., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/180,715
(22) PCT Filed: May 23, 1997
(86) PCT No.: PCT/JP97/01739
  § 371 Date: Nov. 13, 1998
  § 102(e) Date: Nov. 13, 1998
(87) PCT Pub. No.: WO97/44190
  PCT Pub. Date: Nov. 27, 1997

(30) Foreign Application Priority Data

May 23, 1996 (JP) .................................................. 8-150500

(51) Int. Cl.[7] ......................... B32B 15/08; B32B 27/08; B32B 27/36; B32B 31/08; B32B 31/20
(52) U.S. Cl. ..................... 428/212; 428/458; 428/480; 428/910; 428/412; 156/164; 156/229; 156/309.6; 156/309.9; 156/321; 156/322; 156/324; 156/494; 156/499; 156/543; 156/555
(58) Field of Search ................................. 156/164, 229, 156/309.6, 309.9, 321, 322, 324, 494, 499, 543, 555; 428/412, 458, 480, 910, 212

(56) References Cited

U.S. PATENT DOCUMENTS 4,362,775 * 12/1982 Yabe et al. .............................. 428/213
4,980,210 * 12/1990 Heyes .................................. 428/35.9
5,149,389 * 9/1992 Heyes et al. ........................ 156/272.4
5,876,851 * 3/1999 Matsumura et al. .................. 428/412
5,985,088 * 11/1999 Couillard et al. ..................... 156/324

FOREIGN PATENT DOCUMENTS

| 796721 | * 9/1997 | (EP) . |
| 3-254936 | 11/1991 | (JP) . |
| 4-201237 | 7/1992 | (JP) . |
| 7-214742 | 8/1995 | (JP) . |

OTHER PUBLICATIONS

Derwent 1996–287001, abstract of WO 96/17721 and EP 796,721 A1 Mar. 1998.*

* cited by examiner

Primary Examiner—D. S. Nakarani
Assistant Examiner—Ramsey Zacharia
(74) Attorney, Agent, or Firm—Browdy and Neimark (57) ABSTRACT

A resin laminated metallic sheet having excellent adhesion during forming, corrosion resistance, and impact resistance is continuously manufactured at high speed with consistent properties is constantly kept at a selected and variable traveling speed of the metallic sheet by controlling the orientation of resin film after lamination, heating the continuously traveling metallic sheet, laminating resin films on both sides of the heated metal sheet using laminating rolls, and thereafter deflecting the traveling direction of the resin laminated metallic sheet using a deflector roll disposed movably in a direction perpendicular to the direction at a right angle from traveling direction of the metallic sheet, and further, differentiating a contacting period of time in which each surface of the resin laminated metallic sheet is contacting each of the laminating rolls, or differentiating an amount of the heat of each surface portion of the resin laminated metallic sheet lost by the cooling effect due to the contact of the resin laminated metallic sheet with the laminating roll.

9 Claims, 5 Drawing Sheets

THERMOPLASTIC RESIN-COATED METAL PLATE, AND METHOD OF AND APPARATUS FOR MANUFACTURING THE SAME

FIELD OF THE INVENTION

The present invention relates to a manufacturing method for thermoplastic resin laminated metallic sheet and a thermoplastic resin laminated metallic sheet manufactured using this manufacturing method, and manufacturing apparatus therefor. More particularly, it relates to manufacturing method for thermoplastic resin laminated metallic sheet (hereinafter, simply referred to as resin laminated metallic sheet), in which biaxially oriented thermoplastic resin films are made to contact both surfaces of a heated metallic sheet continuously traveling and the orientation coefficients of the thermoplastic resin films (hereinafter, simply referred to as resin films) after pressed to adhere to the metallic sheet are controlled within preferable ranges corresponding to which side of the metallic sheet the resin film is laminated on, and thermoplastic resin laminated metallic sheet using manufactured this manufacturing method as well as manufacturing apparatus therefor.

BACKGROUND TECHNOLOGY

In recent years, a larger quantity of materials for metallic sheet laminated on both surfaces thereof with thermoplastic resin films such as polyester resin film have been used for can stocks such as drawn can and draw;n and stretch formed can or the like which are subjected to severe working. Today, cans formed by drawing and stretch forming and further ironing is developed from the economical view point. In general, when a severe forming is carried out on a metallic sheet laminated with oriented resin film, the orientation coefficient of the resin film after lamination should be reduced to a small value so as to improve the formability. Otherwise, the resin film would be peeled off or have cracks caused. Namely, a considerable part of the orientation of the resin film needs to be lost by the heat when the resin film is thermally bonded to a metallic sheet. A film for forming the outside wall of can body requires not so great corrosion resistance and impact resistance but requires higher formability than a film for forming the inside wall of can body when formed into a can. On the other hand, the film for forming the inside wall of can body needs greater corrosion resistance and impact resistance, since the film of the inside wall of can body comes into direct contact with the content after packed and sometimes would be damaged by outer impact.

In order to satisfy both the requirements for the properties of the inside and outside walls of can body, a certain extent of the orientation should be retained in the resin film to form the inside wall of can body, while preferably not so much of the orientation is retained in the resin film to form the outside wall of can body.

When a resin laminated metallic sheet having properties bearable to severe forming is produced using the conventional manufacturing method, it is necessary to control various manufacturing conditions such as heating temperature of metallic sheet, the composition of thermoplastic resin film to be laminated, degree of orientation of resin film, melting temperature of resin, laminating speed, laminating roll pressure or the like.

Figure 3:
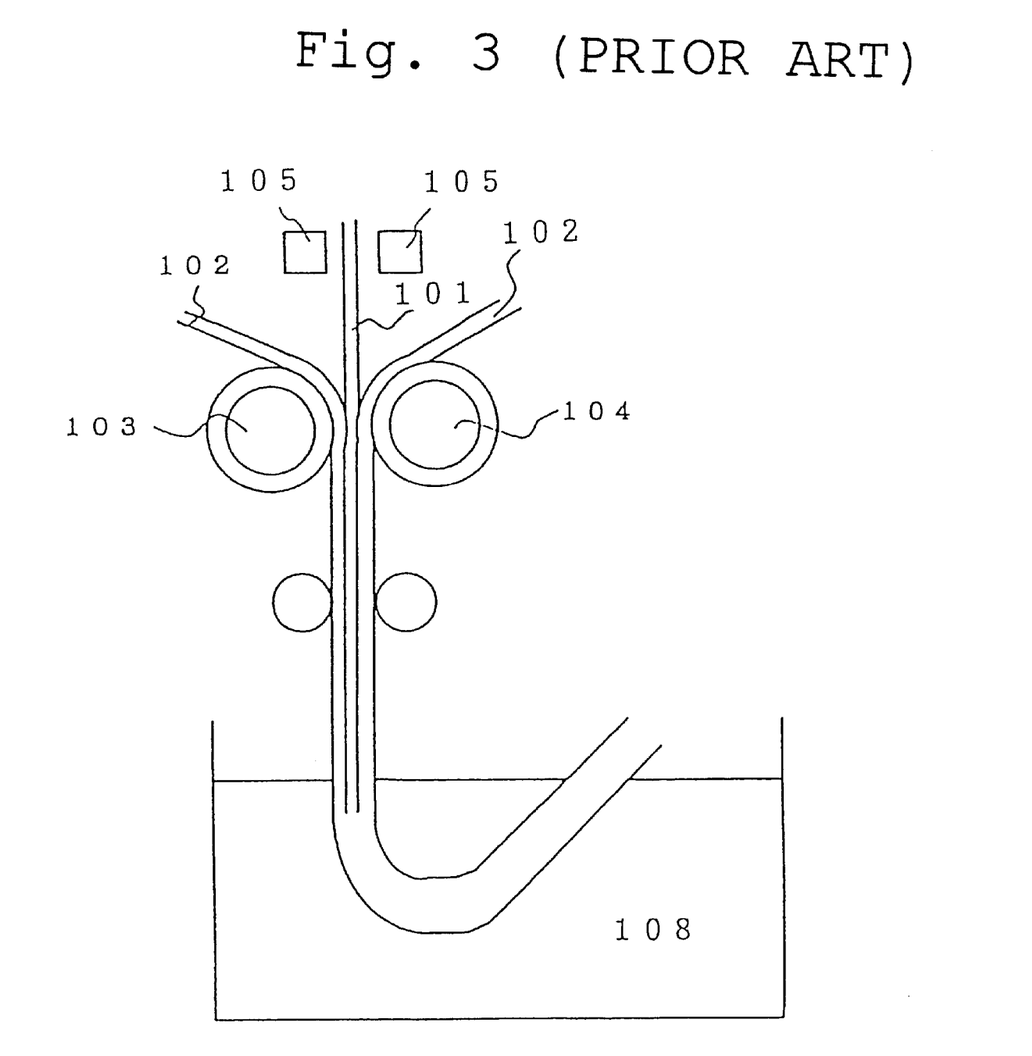
FIG. 3 is a schematic view showing a manufacturing apparatus for manufacturing a laminated metallic sheet employing a conventional method.

FIG. 3 shows a manufacturing method for resin laminated metallic sheet by a conventional art. As known by Laid-Open Japanese Patent Hei 4-201237, for example, a resin laminated metallic sheet is manufactured by a method in which thermoplastic resin film 102 is made to contact both surfaces of metallic sheet 101 heated in oven 105, pressed to metallic sheet 101 using a couple of laminating rolls (nip rolls) 103 and 104, thermally bonded to metallic sheet 101, a part of resin film 102 near metallic sheet 101 being melted by the heat of metallic sheet 101, cooled to a room temperature in quenching tank 108 and then dried. In such a manufacturing method of resin laminated metallic sheet, thickness of the melted portion of resin film 102 (thickness of melting layer), degree of orientation, adhesion strength to metallic sheet or the like can be controlled to some extent by taking account of heating temperature of metallic sheet, distance between oven 105 and laminating rolls 103, 104, travelling speed of metallic sheet, properties of resin such as composition, thickness, degree of orientation, or melting temperature, and suitably selecting manufacturing conditions for the lamination of resin film.

Figure 4:
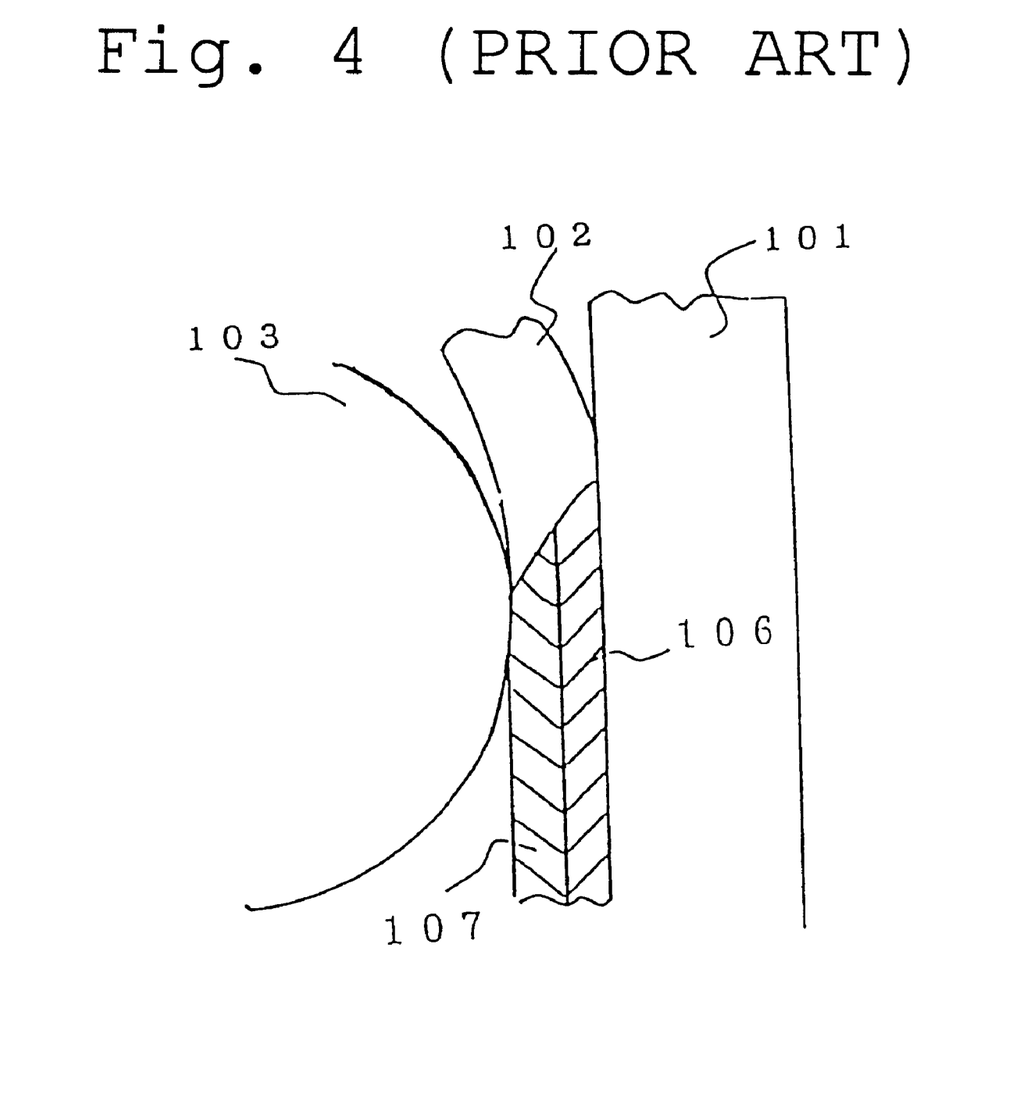
FIG. 4 is a partially enlarged cross section of FIG. 3.

In the above mentioned conventional method, as shown in FIG. 4, in a case where resin film 102 is laminated on metallic sheet 101 having been heated in oven 105, when resin film 102 and metallic sheet 101 are pressed by laminating rolls 103, 104 wherein metallic sheet 101 is first heated in oven 105, heat is transferred from metallic sheet 101 of high temperature to laminating rolls 103, 104 of low temperature through resin film 102. Accordingly, melting layer 106 (adjacent unmelted layer 107) is formed at a surface of resin film 102 contacting the metallic sheet and at the same time resin film 102 and metallic sheet 101 are bonded together by the laminating roll pressure. After passing through between the laminating rolls 103, 104, they are free from the pressure, and the surface of laminate resin film is naturally cooled, while the heat of the metallic sheet is transferred to the whole of the resin film, thereby controlling the degree of orientation wholly in the resin film. When both members are cooled by the laminating rolls, an oriented layer is retained on the outermost surface of the resin film. Accordingly, if the travelling speed of metallic sheet is high, cooling by laminating rolls is insufficient. Therefore, it is necessary to lower the heating temperature of metallic sheet to control the degree of orientation of resin film. Thus, it is difficult to continuously manufacture a resin film laminated metallic sheet at high speed.

On the other hand, in a case where resin film is continuously laminated on metallic sheet at high speed, a melting layer of resin film to be laminated should be thick to some extent so as to have excellent adhesion during forming. One of the methods therefor may be to raise the heating temperature of metallic sheet. But in this case, cooling effect by laminating roll is insufficient, so that almost whole of the resin film is melted and consequently the strength of resin film is decreased. Moreover, another problem is caused that if the layer of resin film laminated on a metallic sheet, the whole of which is once melted when laminated, forms an inside wall of a can after formed, the laminated resin layer has easily cracks to cause corrosion of the can body by any outer impact when or after the content is packed in the can.

Thus, it would be possible even by the conventional method to manufacture a resin laminated metallic sheet having adhesion during forming fit for a laminate can which is formed by severe forming but its laminated resin layer is not peeled off, if only properties of the resin film to be laminated such as composition, thickness, degree of orientation, melting temperature are taken into account, the respective resin films for inside and outside wall of can are suitably selected, and manufacturing conditions such as heating temperature of metallic sheet, supplying speed of metallic sheet and resin film, pressure of laminating rolls are properly predetermined. However, it is extremely difficult to continuously manufacture such a resin film laminated metallic sheet at high speed. Moreover, when the traveling speed of metallic sheet is increased or decreased to perform the continuous manufacturing, the laminated resin film has uneven orientation, which results in the partial peeling-off of the laminated resin film when the laminate is intensely formed. Consequently, the economical efficiency and productivity of the resin laminated metallic sheet which should have superior adhesion during forming and corrosion resistance is decreased and the continuous manufacturing thereof cannot be smoothly performed.

It is an object of the present invention to solve the problems encountered in the prior art resin laminated metallic sheet, the manufacturing method and apparatus therefor, and to provide a resin laminated metallic sheet having more excellent adhesion during forming, corrosion resistance, impact resistance, and so on and also manufacturing method and manufacturing apparatus for continuously producing the same at high speed while ensuring the qualities thereof even when traveling speed of metallic sheet is varied.

DISCLOSURE OF THE INVENTION

The manufacturing method for a thermoplastic resin laminated metallic sheet of the present invention is characterized by the steps of:

heating a continuously travelling metallic sheet, contacting both surfaces of the metallic sheet with thermoplastic resin film having orientation, pressing the metallic sheet and the thermoplastic resin film using a couple of laminating rolls by pinching them to bond together, and thereafter moving a deflector roll, which is disposed at a downside of the laminating rolls so as to contact one of the surfaces of the metallic sheet laminated with thermoplastic resin and movable in a direction perpendicular to the traveling direction of the laminated metallic sheet, to said direction perpendicular to the traveling direction of the metallic sheet and to a direction opposite to an initial position of the deflector roll, so as to bias the traveling direction of the laminated metallic sheet to thereby differentiate the contacting distance, or contacting period of time, in which each surface of the resin laminated metallic sheet is contacting either one of the laminating rolls, or differentiate the amount of the heat of each surface portion of the resin laminated metallic sheet, which is lost by the cooling effect due to the contact with the laminating rolls, so that the orientation coefficients of the outermost layer of the thermoplastic resin film after laminated are controlled to be different with regard to each surface side of the metallic sheet.

Further, the manufacturing method for a thermoplastic resin laminated metallic sheet of the present invention is characterized by the deflector roll disposed to make the oriented thermoplastic resin film contact both surfaces of the metallic sheet, wherein the orientation coefficient of the outermost layer of one side resin film contacting the deflector roll is smaller than that of the outermost layer of the opposite side resin film not contacting the deflector roll.

Furthermore, the manufacturing method for a thermoplastic resin laminated metallic sheet of the present invention is characterized in that both surfaces of the metallic sheet continuously traveling are laminated with thermoplastic resin films having different melting temperatures, respectively, and also in that both surfaces of the metallic sheet continuously traveling are laminated with resin films having different heat-setting temperatures, respectively, said resin films are prepared by melting thermoplastic resin, elongating and orienting the same in biaxial directions, and thereafter thermally setting the same respectively at different temperatures.

Still further, the present invention includes a thermoplastic resin laminated metallic sheet produced by laminating a thermoplastic resin film on a metallic sheet using the above mentioned manufacturing method, wherein when the orientation coefficient of one surface portion of a thermoplastic resin film contacting the metallic sheet is represented by n1A, the orientation coefficient of the other surface portion of the thermoplastic resin film not contacting the metallic sheet is represented by n2A, said thermoplastic resin film being laminated on one side (A) of the metallic sheet, and the orientation coefficient of one surface portion of a thermoplastic resin film contacting the metallic sheet is represented by n1B, the orientation coefficient of the other surface portion of the thermoplastic resin film not contacting the metallic sheet is represented by n2B, said thermoplastic resin film being laminated on the other side (B) of the metallic sheet, said thermoplastic resin film has the orientation coefficients in the following ranges:

n1A is 0 to 0.04, n1B is also 0 to 0.04, n2A is 0.02 to 0.10, and n2B is 0 to 0.10, and n1A<n2A, n1B<n2B, n2B<n2A.

The thermoplastic resin laminated metallic sheet of the present invention is further characterized in that said thermoplastic resin is polyethylene terephthalate resin, copolyester resin mainly consisting of ethylene terephthalate recurring unit, polybutylene terephthalate resin, or copolyester resin mainly consisting of butylene terephthalate recurring unit, or blended polyester resin having at least two resins selected from them to blend, or plural-layered laminate polyester resin having at least two resins selected from them, or said thermoplastic resin is a double-layered resin composed of an upper layer and a lower layer, the upper layer including polyethylene terephthalate resin, copolyester resin mainly consisting of ethylene terephthalate recurring unit, polybutylene terephthalate resin, or copolyester resin mainly consisting of butylene terephthalate recurring unit, or blended polyester resin having at least two resins selected from them to blend, and the lower layer including blended resin of poly carbonate resin and one of the thermoplastic resins forming said upper layer.

The present invention includes also manufacturing apparatus for the thermoplastic resin laminated metallic sheet comprising:

heating means for heating metallic sheet continuously traveling, supply means, disposed at a downside in the advance direction of the metallic sheet, for supplying thermoplastic resin film onto both sides of the heated metallic sheet, a couple of laminating rolls disposed at a downside of the supply means so as to make the thermoplastic resin films contact both sides of the metallic sheet by pinching both members to press them for lamination, a deflector roll disposed at a downside of the laminating rolls so as to contact one side thermoplastic resin film laminated on the metallic sheet and movable in a direction perpendicular to the traveling direction of the metallic sheet, and cooling means disposed at a downside of the deflector roll to cool the laminated metallic sheet with thermoplastic resin.

BEST MODE FOR CARRYING OUT THE INVENTION

The manufacturing method for resin laminated metallic sheet of the present invention comprises the steps of: heating a metallic sheet continuously traveling, adhering resin film to both surfaces of the metallic sheet using a couple of laminating rolls under its roll pressure to laminate them, and, thereafter moving a deflector roll, movably disposed in a direction perpendicular to the traveling direction of the metallic sheet, to bias the traveling direction of the resin laminated metallic sheet. As a result, contacting distance or contacting period of time, in which each of the surfaces of resin laminated metallic sheet is contacting the laminating roll, has a difference between said surfaces of the resin laminated metallic sheet, so that the resin films are each deprived of a different amount of the heat from their respective surface portions by the cooling effect due to contacting the laminating rolls. Consequently, the orientation of the resin films after laminated can be controlled. Thus, using the manufacturing method of the present invention, it is possible to produce a resin laminated metallic sheet whose resin layers have different orientation coefficients between the surface portion contacting the metallic sheet and the outside portion not contacting the metallic sheet, respectively. The method of the present invention can therefore provide a resin laminated metallic sheet having enough formability to bear severe forming.

At first, the manufacturing method and apparatus for a resin laminated metallic sheet of the present invention will be explained in detail referring to Figures.

Figure 1:
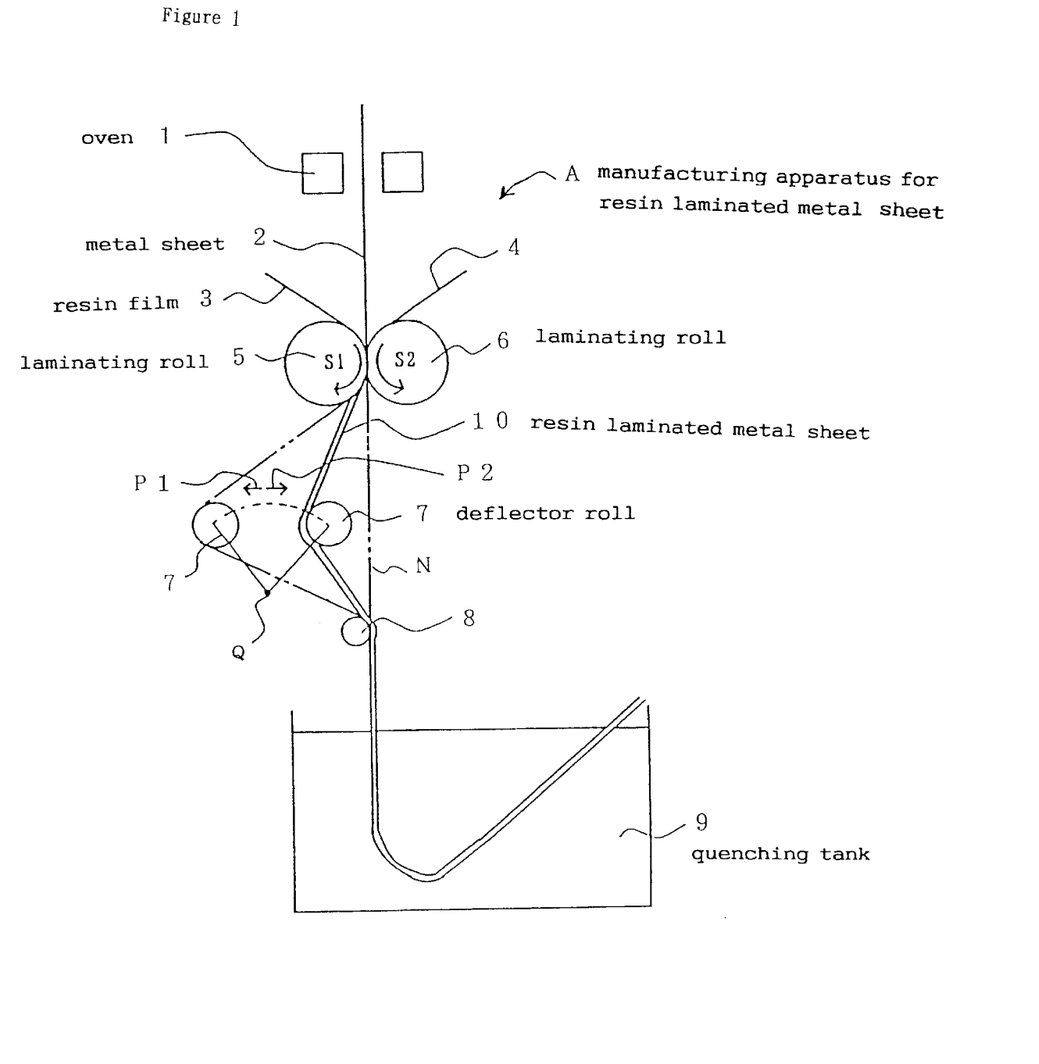
FIG. 1 is a schematic view showing one embodiment of the manufacturing apparatus used for manufacturing a resin laminated metallic sheet of the present invention.
Figure 2:
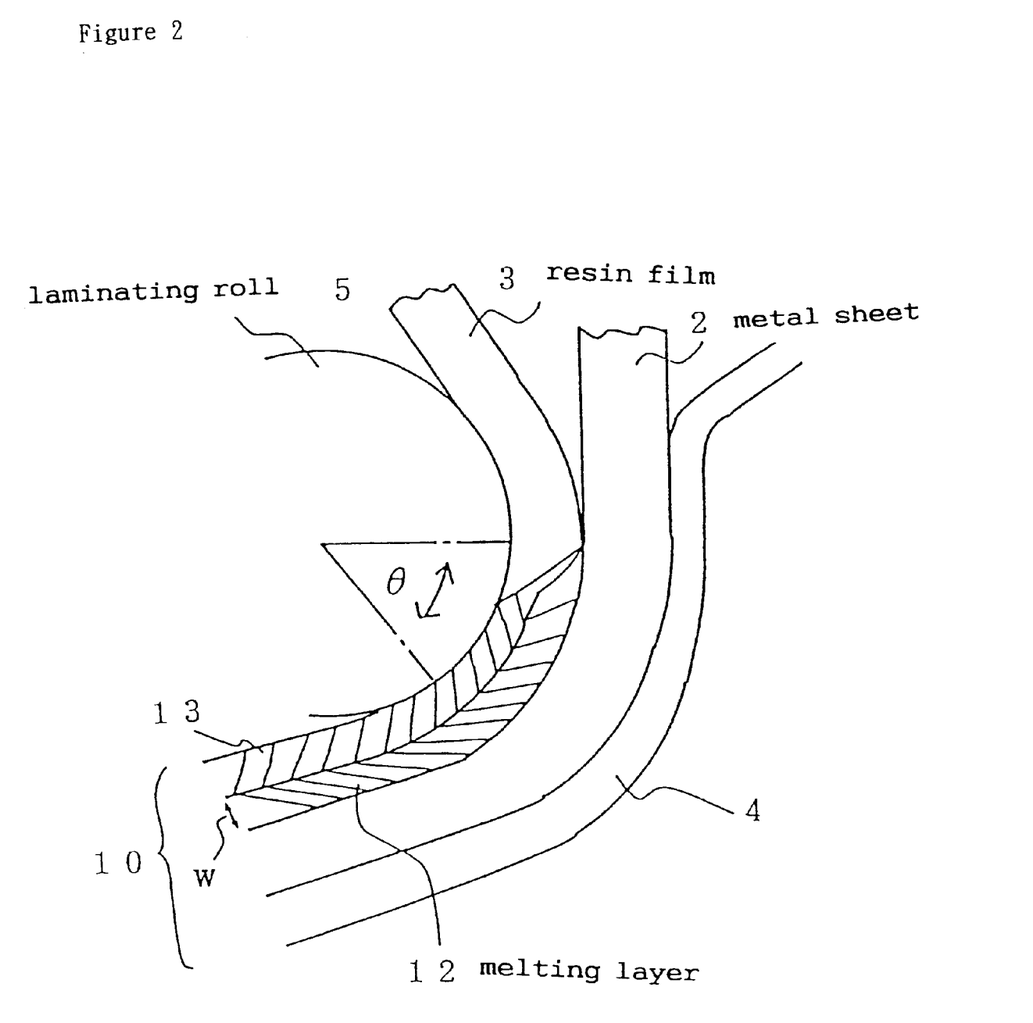
FIG. 2 is a partially enlarged cross section of FIG. 1.

FIG. 1 is a schematic view showing one embodiment of the manufacturing apparatus used for manufacturing a resin laminated metallic sheet of the present invention, and FIG. 2 is a partially enlarged cross section of FIG. 1.

In the manufacturing apparatus for a resin laminated metallic sheet shown in FIG. 1, mark 1 represents heating means for continuously heating metallic sheet 2 travelling from the upper part to the lower part on the figure, and a couple of laminating rolls 5, 6 for pressing resin films 3 and 4 to thermally bond to the heated metallic sheet 2 are disposed in a downside of the heating means. In a slightly downward portion of this laminating roll, deflector roll 7 is disposed to contact one of the surfaces of resin laminated metallic sheet 10, rotatable and movable in directions as indicated by arrows P1 and P2 perpendicular to the travelling direction of resin laminated metallic sheet 10. Further, in a downside of this deflector roll 7, guide roll 8 is rotatably disposed. The rotation axes of laminating rolls 5, 6, deflector roll 7 and guide roll 8 are parallel to each other. In a downside of guide roll 8, quenching tank 9 is disposed for cooling resin laminated metallic sheet 10 to room temperature.

Figure 5:
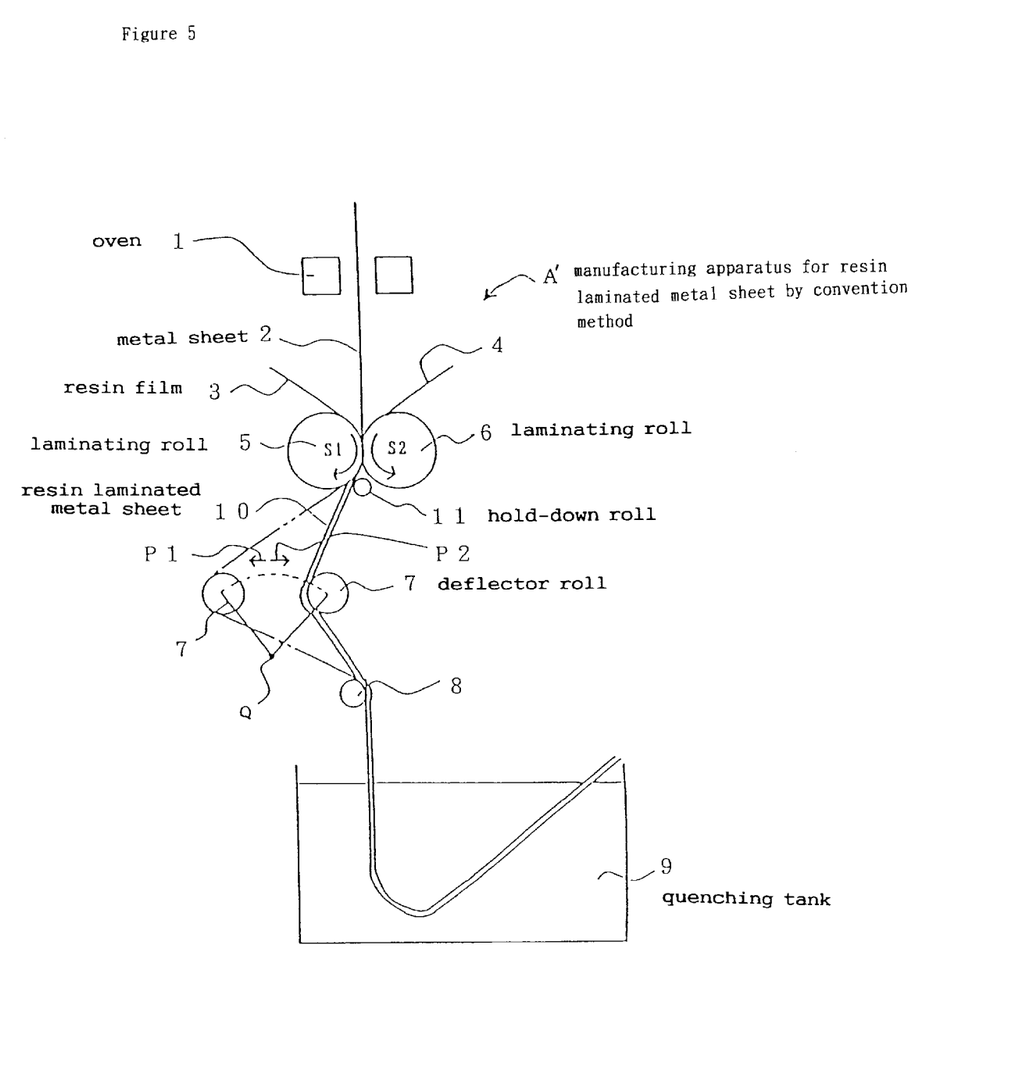
FIG. 5 is a schematic view showing another embodiment of the manufacturing apparatus used for manufacturing a resin laminated metallic sheet of the present invention.

Manufacturing apparatus A' shown in FIG. 5 has hold-down roll 11 for pushing resin laminated metallic sheet 10 to laminating roll 5 added to manufacturing apparatus A shown in FIG. 1. This hold-down roll 11 is rotatably disposed and parallel to laminating roll 5.

As heating means 1, a known device such as high frequency heating oven is used. Other heating means such as heating rollor induction coil for heating are also applicable. Laminating rolls 5 and 6 act as nip rolls for pinching and pressing metallic sheet 2 passing through between them and resin film 3, 4 inserted between them. For the laminating rolls, a known device is used. Usually, both laminating roll 5 and 6 can synchronously be rotated in directions indicated by arrows S1 and S2, respectively, so that the resin laminated metallic sheet travels downward, and the clearance between these laminating rolls and their rotation speed are adjustable.

Deflector roll 7 has its both ends supported by bearings (not shown) and the bearings are each synchronously movable and adjustable in the directions of arrow P1 or P2 using a control cylinder or the like. Positions of the bearings are normally adjusted according to a predetermined laminating condition, and a fixed position thereof is selected for operating the laminating rolls. But also, they are so adjusted as to move in the direction of P1 or P2 in accordance with the laminating speed during the operation. Furthermore, they are arranged to move straight and reciprocatingly in a direction to perpendicular to the surface of the laminate metallic sheet, or arranged to rotate about an axis Q positioned below (or above) their axes and parallel to them, that is, they may be movable in an arc line as shown by the imaginary line.

Guide roll 8 has its both ends supported by bearings (not shown) and the bearings are each fixed to a frame or the like. The guide roll 8 is arranged at such a position as to contact common tangential line N of a couple of laminating rolls 5, 6 (see FIG. 1). Not shown, but laminated metallic sheet 10 taken out from quenching tank 9 is driven downward by another nip roll. Therefore, tension is applied to laminated metallic sheet 10, and suitable tension is also applied to laminated metallic sheet 10 running between a couple of laminating rolls 5, 6 and guide roll 8.

Manufacturing apparatus A for resin laminated metallic sheet constructed as described above is used as follows.

At first, resin films 3, 4 supplied from resin film supply means, not shown, are made to contact both sides of metallic sheet 2 having been heated to a predetermined temperature by heating means 1 and they are pressed to bond together between laminating rolls 3 and 4. Then, thus laminated metallic sheet with resin films 10 is passed on the left side of deflector roll 7 which is deviated to the left side from common tanqential line N as shown in FIG. 1, and then passed on the right side of guide roll 8 to thereby make its running direction back to the original travelling direction. The deviation distance of deflector roll 7 is suitably selected according to the property of the resin film to be laminated, heating temperature of metallic sheet, desired orientation coefficient of the resin layer to be laminated and forming conditions therefor. Then, the laminated metallic sheet is guided downward into quenching tank 9.

Since laminated metallic sheet 10 coming out from laminating rolls 5,6 travels in a zigzag line, it contacts one laminating roll 5 by a predetermined winding angle (contacting angle) θ. Winding angle θ becomes larger as deflector roll 7 is deviated by a more distance to the left in FIG. 1, while it becomes smaller as it moves to the right. When the deviation distance of deflector roll 7 becomes nil, the winding angle becomes nil, and the laminated metallic sheet travels downward straight as conventional.

Thus, the contacting of the laminated metallic sheet with one laminating roll 5 by predetermined winding angle θ produces the longer cooling period of time for the surface of the laminated metallic sheet contacting laminating roll 5. When provided with hold down roll 11 shown in FIG. 6, further cooling effect is improved.

The increase of cooling period of time also depends on the increase of the pressure applied to resin films 3, 4 and metallic sheet 2. The pressure affects the cooling effect not only on resin film 3 contacting one laminating roll 5 but also on resin film 4. The smaller the pressure and the longer the contacting period of time with laminating roll 5, the greater the total quantity of conducted heat. The longer the cooling period of time is, the more the heat is conducted from the heated metallic sheet 2 to laminating roll 5, which allows the temperature of metallic sheet 2 further to be lowered to thereby decrease the thickness W of melting layer 12 of the resin layer contacting the metallic sheet. As a result, the laminated resin film has a layer with enough orientation to have excellent formability provided on a side portion contacting the metallic sheet. When thus laminated resin film forms an inside wall of can body, desired adhesion during forming and corrosion resistance can be obtained.

As explained above, provided that a resin film is laminated on a metallic sheet at the same laminating speed as conventional, the adhesion during forming and the corrosion resistance of the laminated resin layer is more excellent if using the method of controlling the amount of the heat conducted from metallic sheet 2 to the laminating rolls, according to the present invention. Conversely speaking, provided that the adhesion during forming of the laminated resin layer is enough even of the same extent as that conventional, the laminating speed of the resin film can also be increased, if using the method of the present invention. That is, moving deflector roll 7 in P1 direction in FIG. 1 to wind the laminated metallic sheet round laminating roll 5 allows laminated metallic sheet 10 immediately after laminated to contact laminating roll 5 longer and cooling by laminating roll 5 fully effects on the resin layer. As a result, even if the travelling speed of metallic sheet 2 is increased, metallic sheet 2 is contacting laminating roll 5 for enough period of time, so that the entirety of resin film 3 to be laminated is not melted. Namely, an un-melted layer, in other words, a layer 13 having orientation can reliably be retained in the outer surface of the laminated resin film. Accordingly, even if laminated at high laminating speed, the resin film is provided with melting layer 12 having enough adhesion during forming and oriented layer 13 having enough corrosion resistance at the outermost portion thereof. Thus, the adhesion during forming and corrosion resistance necessary to the inner wall of can body can be attained. On the other hand, the other side of the resin laminated metallic sheet immediately after laminated, which is not wound round laminating roll 5, is retarded to cool off so that a melted layer increases and the orientation of the outermost portion of the resin film decreases. Accordingly, this side of the resin film can be provided with formability for severe forming necessary to the outer wall of can body.

If the relationship between various factors such as heating temperature of metallic sheet, travelling speed of metallic sheet, resin composition, thickness and orientation coefficient of resin film to be laminated, winding angle of resin laminated metallic sheet round laminating roll 5, which is determined by the deviation distance of deflector roll 7 in P1 direction, thickness and orientation coefficient of the resin layer contacting the metallic sheet, and orientation coefficient of the outermost portion of the resin film, are beforehand grasped into a reference date, it is easy to control, using this reference date, the thickness of melting layer of resin film, orientation coefficient of resin layer contacting the metallic sheet and that of the outermost resin layer, even when the laminating speed of is changed.

Next, the state of resin layer after laminated on metallic sheet will be explained as one of the features of the present invention. When the resin film is made to contact the metallic sheet having been heated to a temperature more than the melting temperature of the resin and pressed to bonding, the orientation of the resin film is destroyed by the heat conducted from the metallic sheet, and the more orientation is lost in a portion nearer to the metallic sheet, while the more orientation is retained in a portion nearer to the outermost surface remote from the metallic sheet. In the resin laminated metallic sheet of the present invention, it is essential that when the orientation coefficient of one surface portion of the resin film directly contacting the metallic sheet is represented by n1A, the orientation coefficient of the outermost surface portion is represented by n2A, the resin film being laminated on one side (A) of the metallic sheet, and the orientation coefficient of one surface portion of the resin film directly contacting the metallic sheet is represented by n1B, the orientation coefficient of the outermost surface portion of the resin film is represented by n2B, the resin film being laminated on the other side (B) of the metallic sheet, these orientation coefficients are determined within the following ranges: n1A as well as n1B is 0 to 0.04, n2A is 0.02 to 0.10, n2B is 0 to 0.10, and n2B<n2A, and also essential that when this resin laminated metallic sheet is formed into can body, the side (A) forms an inside wall and the side (B) forms an outside wall of can body, respectively.

In the resin layer laminated on the metallic sheet, in a case where the orientation coefficients n1A and n1B exceed 0.04, the laminated resin layer is easily peeled off from the metallic sheet in both sides of can body when the resin laminated metallic sheet is subjected to severe forming such as drawing and stretch forming. With the orientation coefficient not more than 0.04, the resin layer is not peeled off, so the orientation coefficients n1A and n1B are required to be not more than 0.04, This resin layer directly contacting the metallic sheet corresponds to a melting layer formed by heat, which is given a adhesion during forming. Enough adhesion strength is obtained as far as the orientation coefficient thereof is within the range of 0 to 0.04 for both sides of can body. While, measuring method for orientation coefficient is described later in detail, the orientation coefficient is determined from refractive index and is a mean value from the outermost surface to 5 μm depth of a resin layer peeled off from metallic sheet. In other words, even if the orientation coefficient of the outermost surface of the resin layer contacting the metallic sheet is in fact nil, namely un-oriented, it will exceed 0 when an oriented portion exists within 5 μm depth. In the resin covered metallic sheet of the present invention, n1A and n1B are determined as 0 to 0.04 based on the above mentioned reasoning.

Further next, in order to obtain formability, corrosion resistance and impact resistance of the resin covered metallic sheet of the present invention, it is necessary to determine the orientation coefficients of the outermost surface portions of resin layers laminated on both sides of the metallic sheet: n2A is 0.02 to 0.10 and n2B is 0 to 0.10, and n2B<n2A.

In a case where the orientation coefficient n2A at the outermost surface portion of the resin layer is less than 0.02, the permeation resistance of the whole resin layer to the packed content is remarkably decreased and this is particularly unfavorable for the inside wall of can body directly contacting the packed content. In addition, in a case where both of the orientation coefficients n2A and n2B exceed 0.10, even if the orientation coefficient n1A or n1B of the resin portion directly contacting the metallic sheet is less than 0.04, cracks are numerously caused in the upper layer of the resin film when the resin laminated metallic sheet is severely formed, and the thus produced can is not for practical use. Accordingly, it is at first essential that the orientation coefficient n2A of the outermost surface portion is within the range of 0.02 to 0.10, Secondly, it is necessary for the resin laminated metallic sheet of the present invention to be severely formed that n2B is within the range of 0 to 0.10 and n2B<n2A, and this resin laminated metallic sheet should be formed into a can with one surface portion having n2A forming an inside wall of can body and the other surface portion having n2B forming an outside wall thereof. Namely, when a resin laminated metalic sheet is formed into a can by severe forming such as drawing and stretch forming, a resin film forming an outside wall of can body needs more formability, with its orientation coefficient rather small, but the other resin film forming an inside wall of can body needs extremely high corrosion resistance and impact resistance, with its orientation coefficient rather large. Supposing both the surface portions of the resin films have the same orientation coefficient, or n2A<n2B, any of properties of the resin film for forming the inside and outside walls of can body would be neglected.

The reason why n1A<n2A and n1B<n2B is defined is: the resin film to be laminated is given heat to melt from the surface contacting the metallic sheet heated more than the melting temperature of the resin according to the manufacturing method of the present invention, the orientation coefficients necessarily become as described above. Namely, in the resin layer laminated on the metallic sheet, the orientation coefficient gradually increases from the surface contacting the metallic sheet to the outermost surface in its thickness direction.

The orientation coefficient of the resin film to be laminated itself is also an important factor in order to obtain a resin laminated metallic sheet having the different orientation coefficient of the resin layer on each side of the metallic sheet. In a case where the orientation coefficient of the resin film to be laminated exceeds 0.17, it is extremely difficult to make the orientation n2A and n2B at the outermost surface of the resin layers less than 0.15 and make n1A and n1B at the portion directly contacting the metallic sheet less than 0.10 when the resin film is made to contact the metallic sheet heated more than the melting temperature of the resin. Accordingly, the orientation coefficient of the resin film to be laminated itself is preferably not more than 0.17, more preferably around 0.15.

The orientation coefficient n1A, n1B, n2A and n2B of the resin layers contacting the metallic sheet and the outermost surface portion after the resin film is laminated on the metallic sheet, which are important factors in the present invention, are determined by the following method. That is, the orientation coefficient of the resin film to be laminated can be calculated by the following formula measuring the refractive indexes in the lengthwise direction, the width wise direction and the thickness direction using Abbe's refractometer.

Orientation coefficient=(A+B)/2−C
A: refraction index in the lengthwise direction
B: refraction index in the widthwise direction
C: refraction index in the thickness direction In case of the resin laminated metallic sheet, the orientation coefficient is calculated by the above-described formula measuring the refractive indexes in the lengthwise direction, the width wise direction and the thickness direction of the resin layer at the portion contacting the metallic sheet and at the outermost surface in the same manner as described above, after the resin film alone is peeled off by dipping the resin laminated metallic sheet in hydrochloric acid solution and chemically dissolving the metallic sheet surface.

In the resin covered metallic sheet of the present invention, the orientation coefficient of the laminated resin film indicates the oriented degree of the crystal, however, when pigment or the like is mixed into the resin, it is sometimes difficult to measure the orientation coefficient. In such a case, it can be calculated using X-ray diffraction method, IR method (Infrared method) and so on. The measurement of the orientation coefficient of polyethylene terephthalate film by X-ray diffraction method will be explained as an example.

The orientation degree of polyethylene terephthalate film can be determined by measuring the X-ray diffraction intensity of (100) plane as an index, namely the X-ray diffraction intensity of (100) plane when 2θ=26°. The X-ray diffraction intensity is correlative with the orientation coefficient so that the oriented degree of the crystal S can be obtained by measuring the X-ray diffraction intensity of (100) plane even in the pigmented resin film based on the predetermination of the correlation between the X-ray diffraction intensity and the orientation coefficient in the resin film having the same resin composition without pigment.

In order to measure the oriented degree of the resin at a portion from the outermost surface to 5 μm depth of the laminated resin film, only an entry depth of the X-ray entering into the resin film is set to 5 μm in the above-described X-ray diffraction method, and a thin film X-ray diffraction apparatus facilitates the measurement. Namely, an X-ray is entered into the laminated resin film at a low angle. By setting as 2θ=26° at the measurement, the oriented degree of the crystal on (100) plane at the outermost surface portion of the laminated resin film may be obtained. However, it is also necessary to determine beforehand the correlation between the X-ray diffraction intensity and the orientation coefficient in the resin film having the same resin composition without pigment.

In the present invention, a resin film to be laminated on both sides of a metallic sheet is preferably a film of polyethylene terephthalate resin, copolyester resin mainly consisting of ethylene terephthalate recurring unit, poly-butylene terephthalate resin, or copolyester resin mainly consisting of butylene terephthalate recurring unit, or blended polyester resin having at least two resins selected from them to blend, or plural-layered laminate polyester resin having at least two resins selected from them, or double layered resin composed of an upper layer and a lower layer, the upper layer including polyethylene terephthalate resin, copolyester resin mainly consisting of ethylene terephthalate recurring unit, poly-butylene terephthalate resin, or copolyester resin mainly consisting of butylene terephthalate recurring unit, or blended polyester resin having at least two resins selected from them to blend, and the lower layer including blended resin of poly carbonate resin and one of the thermoplastic resins for the above-described upper layer. These resins are formed into a film by a known extruder, thereafter biaxially elongated and oriented, and heat set to be used as a biaxially oriented resin film. Additives such as stabilizer, antioxidant, antistatic agent, pigment, lubricant, corrosion inhibitor may be added to resins as cases needs. Particularly, a resin film to be laminated on the side for forming the outside wall of can body may be preferably mixed with white pigment of titanium dioxide in order to make printed designs clearer.

The melting temperature of the resin film to be laminated can be measured using a differential scanning calorimeter (DSC). However, a film of blended resin, for example, has sometimes more than two peaks for melting appearing. In such a case, an approximate melting temperature is determined by multiplying the value of the melting temperature by endthermic value of each peak for melting, adding them and dividing the sum of them by the total endthermic value of all the peak for melting.

The thickness of resin film to be laminated is preferably 5 to 50 $\mu$m, more preferably 10 to 30 $\mu$m. In case of film having thickness less than 5 $\mu$m, the laminated resin film may be broken by severe forming and the corrosion resistance may be deteriorated. Furthermore, it is not only difficult to laminate the resin film having thickness less than 5 $\mu$m in a stable state but also difficult to control the orientation coefficient of the laminated resin film into a desired range. On the other hand, in case of film having thickness more than 50 $\mu$m, it is not preferable from the economical view point compared with epoxy resin paint widely used in the field of the can manufacturing.

The metallic sheet to be used in the resin laminated metallic sheet of the present invention will be explained. A sheet of surface treated steel or aluminum alloy is used therefor. In case of steel sheet, its chemical composition is not particularly limited as far as it is bearable to severe forming. But preferably a steel sheet including low carbon steel sheet of thickness 0.15 to 0.30 mm widely used as a can stock is a substrate and a film of hydrated chromium oxide is formed on it in order to have excellent adhesion during forming with regard to resin film to be laminated, and particularly a steel sheet on which a double layered film consisting of a lower layer of metallic chromium and an upper layer of hydrated chromium oxide is formed, so-called tin free steel, (TFS) is preferable. Furthermore, a steel sheet in which a plating of one of tin, nickel, aluminum or the like, or a double layered plating or an alloy plating consisting of more than one of these metals is formed and the double layered film described above is formed on the plating layer, is also applicable. In case of aluminum alloy sheet, it is not particularly limited as far as it is bearable to severe forming, similarly to the case of steel sheet. However, the aluminum sheet of JIS 3000 series or 5000 series widely used as a can stock is preferable from the view point of economy and formability, and aluminum alloy sheet which is surface treated in known method such as electrolytical treatment in chromic acid solution, immersion in chromic acid solution, etching by acid solution or alkali solution, anodizing are more preferable. Particularly, in a case where the above-described double layered film is formed on the steel sheet or the aluminum alloy sheet, the weight of hydrated chromium oxide is preferably in the range of 3 to 25 mg/m$^2$, more preferably in the range of 7 to 20 mg/m$^2$, from the view point of adhesion during forming of resin film to be laminated. The weight of metallic chromium is not particularly limited, however, it is preferably in the range of 10 to 200 mg/m$^2$, more preferably in the range of 30 to 100 mg/m$^2$, from the view point of adhesion during forming of resin film to be laminated.

Further, it is possible to easily control the desired orientation coefficients of the resin layer at an outermost portion and at a portion contacting the metallic sheet on each side of the metallic sheet not only by laminating resin films having the same properties on the sides of the metallic sheet, respectively, but also by laminating resin films having different melting temperatures on each side of the metallic sheet or laminating resin films having different heat-setting temperatures which is prepared by heating a resin to melt, biaxially orienting the same, and thereafter heat-setting the same. Namely, in a case where two kinds of oriented resin films having different melting temperature are laminated on a metallic sheet heated to a temperature more than the melting temperature of the one resin having the lower melting temperature, the orientation of this resin film having the lower melting temperature is more destroyed than that of the resin film having the higher melting temperature. Also, in a case where two kinds of resin films having different heat-setting temperatures are laminated on a metallic sheet, the orientation of the resin film having the lower heat-setting temperature is more destroyed than that of the resin film having the higher heat set temperature. Thus, the orientation coefficient of the resin layer at the outermost portion and at the portion contacting the metallic sheet can more easily be controlled suitably using these resin films having different properties.

As described above, when resin films 3 and 4 are pressed and thermally bonded to heated metallic sheet 2 which is continuously travelling, and the laminated metallic sheet with resin immediately after laminated is made to wind round laminating roll 5 using deflecting roll 7 movably disposed in directions P1 and P2 as shown in FIG. 1, the following are realized compared with the conventional method.

(1) Even if a resin film is laminated on a metallic sheet at high laminating speed, the orientation coefficients (n1A and n1B) of the laminated resin portions (melting layer) directly contacting the metallic sheet can be controlled within a range of 0 to 0.04, which is enough for excellent adhesion during forming.

(2) Even if a resin film is laminated on a metallic sheet at high laminating speed, the orientation coefficients (n2A and n2B) of the laminated resin portions at the outermost surfaces (surfaceA) of the resin films wound round laminating roll 5 and the other side thereof (surfaceB) not wound round laminating roll 5 can be controlled within a range of 0.04 to 0.10 and n2B<n2A at the same time, and the properties necessary to the inside wall and the outside wall of can body can be obtained.

(3) A resin layer capable of fulfilling the requirements for each side of the resin laminated metallic sheet can be formed at various laminating speed.

The present invention will concretely explained referring to examples and comparative examples, hereinafter.

Example 1 to 3

A biaxially oriented film of copolyester resin (consisting of 88 mole % of terephthalic acid, 12 mole % of isophthalic acid and 100 mole % of ethylene glycol) having thickness of 25 $\mu$m was laminated by heat bonding on each side of TFS (weight of metallic chromium: 105 mg/m$^2$ and that of hydrated chromium oxide: 15 mg/m$^2$ as chromium) sheet having thickness of 0.18 mm using the apparatus shown in FIG. 1. The temperatures of TFS just before entering into laminating roll were controlled to 250, 240 and 232° C. for Example 1, 2 and 3, respectively, so that the orientation coefficient n2A at the outermost surface of the resin film to be laminated on one side (side A: left side of the metallic sheet shown in FIG. 1) to form the inside of can body after laminated was to be 0.06, The temperature of laminating roll that was naturally cooled was kept around 150° C. The traveling speed of TFS was controlled 100, 200 and 400 m/minute for Example 1, 2 and 3, respectively. The deflecting roll 7 was moved in P1 direction in FIG. 1 so that the winding angle of the resin laminated metallic sheet round the laminating roll was to be 20° in each Example.

Example 4 to 6

An aluminum alloy (JIS 5052 H39) sheet having thickness of 0.26 mm was degreased in sodium carbonate solution of 70 g/l at 50° C., followed by being dipped in sulfuric acid solution of 50 g/l at room temperature for the surface to be etched. After that, it was rinsed in water and then dried. On each side of the thus obtained aluminum alloy sheet, a biaxially oriented film of copolyester resin (a double layered film consisting of an upper layer of copolyester having the same resin composition as those of Example 1 to 3 and thickness of 15 $\mu$m and a lower layer of blended resin composed of 45 weight % of a copolyester resin, consisting of 94 mole % of terephthalic acid, 6 mole % of isophthalic acid and 100 mole % of ethylene glycol, and 55 weight % of poly-butylene terephthalate, and having thickness of 10 $\mu$m) was laminated using the apparatus shown in FIG. 1. The temperatures of aluminum alloy sheet just before entering into laminating roll were controlled to 249, 252 and 255° C. for Example 4, 5 and 6, respectively, so that the orientation coefficients at the outermost surface of the resin film to be laminated on one side (side A: left side of the metallic sheet shown in FIG. 1) to form the inside wall of can body after laminated were to be 0.07, 0.05 and 0.03 for Example 4, 5 and 6, respectively. The temperature of the laminating roll that was naturally cooled was kept around 150° C. The traveling speed of aluminum alloy sheet was controlled 200 m/minute. The deflector roll 7 was moved in P1 direction in FIG. 1 so that the winding angle of the resin laminated metallic sheet round the laminating roll was to be 15° in each Example.

Example 7 to 9

A biaxially oriented film of copolyester resin (consisting of 88 mole % of terephthalic acid, 12 mole % of isophthalic acid and 100 mole % of ethylene glycol, and having melting temperature of 228° C. and film heat setting temperature of 190° C.) having thickness of 25 $\mu$m was laminated on one side (A) to form the inside wall of can body of TFS (weight of metallic chromium: 125 mg/m$^2$ and that of hydrated chromium oxide: 12 mg/m$^2$ as chromium) sheet having thickness of 0.18 mm, and a biaxially oriented film of copolyester resin (consisting of 86 mole % of terephthalic acid, 14 mole % of isophthalic acid and 100 mole % of ethylene glycol, and having melting temperature of 228° C. and film heat setting temperature of 190° C.) having thickness of 20 $\mu$m was laminated on the other side (B) to form the outside wall of can body using the apparatus shown in FIG. 1. The temperatures of TFS just before entering into laminating roll were controlled to 250, 240 and 232° C. for Example ample 7, 8 and 9, respectively, so that the orientation coefficient n2A at the outermost surface of the resin film to be laminated on side A after laminated was to be 0.06, The temperature of the laminating roll that was naturally cooled was kept around 150° C. The traveling speed of TFS was controlled 100, 200 and 400 m/minute for Example 7, 8 and 9, respectively. The deflector roll 7 was moved in P1 direction in FIG. 1 so that the winding angle of the resin laminated metallic sheet round the laminating roll was to be 20° in each Example.

Example 10 to 12

The same biaxially oriented film of copolyester resin as those of Example 7 to 9 was laminated on side A of the same TFS sheet as that of Example 7 to 9, and a biaxially oriented film of copolyester resin having the same resin composition, same melting temperature but different film heat setting temperature of 170° C. as those of Example 7 to 9 was laminated on side B using the apparatus shown in FIG. 1. The other conditions were also controlled in the same way as those of Example 7 to 9, The traveling speed of TFS was controlled 100, 200 and 400 m/minute for Example 10, 11 and 12, respectively.

Example 13

A biaxially oriented double layered resin film consisting of an upper layer of having thickness of 15 $\mu$m and the same resin composition as that of Example 1 to 3 and a lower layer of a blended resin, composed of 55 weight % of a copolyester resin consisting of 94 mole % of terephthalic acid, 6 mole % of isophthalic acid and 100 mole % of ethylene glycol and 45 weight % of poly carbonate, and having thickness of 10 $\mu$m was laminated on the same TFS on the same conditions as those of Example 1 to 3, The traveling speed of TFS was controlled 200 m/minute. The deflector roll 7 was moved in P1 direction in FIG. 1 so that the winding angle of the resin laminated metallic sheet round laminating roll was to be 20°.

Comparative Example 1 to 3

The same biaxially oriented copolyester resin film as that of Example 1 to 3 was laminated on the same TFS as that of Example 1 to 3 on the same conditions as those of Example 1 to 3 except for using the apparatus shown in FIG. 4. Namely, after laminated with the resin film, TFS travelled vertically downward without being wound round the laminating roll. The traveling speed of TFS was controlled 100, 200 and 400 m/minute for Comparative Example 1, 2 and 3, respectively.

Comparative Example 4 to 6

The same biaxially oriented copolyester resin film as that of Example 4 to 6 was laminated on either side of an aluminum alloy (JIS 5052 H39) sheet, usually sold on the market, having a chromate film of 5 mg/m$^2$ as chromium and thickness of 0.26 mm using the apparatus shown in FIG. 4. Namely, the resin film was laminated on the aluminum alloy sheet on the same conditions as those of Example 4 to 6 except that after laminated with the resin film, the aluminum alloy sheet travelled vertically downward without being wound round laminating roll. The temperatures of aluminum alloy sheet just before entering into laminating roll were controlled to 249, 252 and 255° C. for Comparative Example 4, 5 and 6, respectively, so that the orientation coefficients n2A at the uppermost surface of the resin film after lamination were to be 0.07, 0.05 and 0.03 for Comparative Example 4, 5 and 6, respectively.

Comparative Example 7 to 9

The same biaxially oriented copolyester resin film as that of Example 7 to 9 was laminated on the same TFS as that of Example 7 to 9 on the same conditions as those of Example 7 to 9 except for using the apparatus shown in FIG. 4. Namely, after laminated with the resin film, TFS travelled vertically downward without being wound round laminating roll. The traveling speed of TFS was controlled 100, 200 and 400 m/minute for Comparative Example 7, 8 and 9, respectively.

The orientation coefficient of the resin layers at the portion contacting the metallic sheet and at the outermost surface in the resin laminated metallic sheets obtained in Example 1 to 13 and Comparative Example 1 to 9 were determined, and they were formed in the manner described below.

At first, they w,ere punched out into blanks having diameter of 160 mm. Each blank was formed into a drawn can having can diameter of 100 mm so that the one side of blank that had contacted laminating roll 5 formed the inside wall of can body. After that it was redrawn into a redrawn can having can diameter of 80 mm. This redrawn can was formed into a drawn and ironed can having can diameter of 66 mm in the composite forming of stretch forming and simultaneous ironing. In this composite forming, the forming was carried out under the conditions that the distance between the redrawing part corresponding to the upper edge portion of can body and the ironing part was 20 mm, the shoulder radius of redrawing die was 1.5 times as much as the sheet thickness and the clearance in the ironing part was 50% as much as the original sheet thickness. After that, the upper edge part was trimmed off using a known method, followed by necked-in forming and flange forming. The peeling-off of the resin layer on the wall of the thus obtained can body and the impact resistance of the inside wall of can body were evaluated in the following manner.

(I) Peeling-off of the resin layer on the wall of can body

The degree of peeling-off of the resin layer on the inside wall and outside wall of the thus obtained can body was observed with naked eyes and evaluated based on the following standard.

⊚: No peeling-off was observed.

○: Slight peeling-off was observed but no problem for practical use.

Δ: Considerable peeling-offs were observed.

X: Whole resin layer was peeled-off at the upper portion of can body.

(II) Impact resistance of the inside wall of can body

After the thus obtained can was packed with water and a rid was corked thereon, it was fallen from the height of 15 cm with its bottom down. Then, the can was opened and water was removed. After that, sodium chloride solution of 3% was refilled in it, and a stainless steel rod was immersed in it as a cathode. Then, the voltage of 6.3 volts was charged between the stainless steel cathode and the can body as an anode. If the metal under the resin layer is even slightly exposed at this charge, the current flows. The degree of exposure was evaluated by the current value (mA).

The results of evaluated properties of the can bodies formed in the above-described manner from the resin laminated metallic sheets obtained in Example 1 to 13 and Comparative Example 1 to 9 were shown in Table 1 to 3.

The marks in Table 1 to 3 represent the descriptions below, respectively.

n1A: orientation coefficient of resin portion contacting side A of metallic sheet n2A: orientation coefficient of resin portion at the outermost surface of resin layer laminated on side A of metallic sheet n1B: orientation coefficient of resin portion contacting side B of metallic sheet n2B: orientation coefficient of resin portion at the outermost surface of resin layer laminated on side B of metallic sheet I: inside wall of obtained can body O: outside wall of obtained can body Ex: Example Co Ex: Comparative Example

TABLE 1

Formability of resin laminated metallic sheet (1)

| | Orientation coefficient of resin layer | | | | Can properties | |
|---|---|---|---|---|---|---|
| | n1A | n2A | n1B | n2B | Peeling-off of film | Impact resistance (mA) |
| Ex 1 | 0.00 | 0.06 | 0.00 | 0.01 | I:⊚, O:⊚ | 0 |
| Ex 2 | 0.00 | 0.06 | 0.00 | 0.02 | I:⊚, O:⊚ | 0 |
| Ex 3 | 0.00 | 0.06 | 0.01 | 0.04 | I:⊚, O:○ | 0 |
| Ex 4 | 0.00 | 0.07 | 0.00 | 0.05 | I:○, O:○ | 0 |
| Ex 5 | 0.00 | 0.05 | 0.00 | 0.03 | I:⊚, O:⊚ | 0 |
| Ex 6 | 0.00 | 0.03 | 0.00 | 0.01 | I:⊚, O:⊚ | 0.3 |
| Ex 7 | 0.00 | 0.06 | 0.00 | 0.01 | I:⊚, O:⊚ | 0 |
| Ex 8 | 0.00 | 0.06 | 0.00 | 0.01 | I:⊚, O:⊚ | 0 |
| Ex 9 | 0.02 | 0.06 | 0.01 | 0.01 | I:○, O:⊚ | 0 |
| Ex 10 | 0.04 | 0.06 | 0.01 | 0.02 | I:○, O:⊚ | 0 |

TABLE 2

Formability of resin laminated metallic sheet (2)

| | Orientation coefficient of resin layer | | | | Can properties | |
|---|---|---|---|---|---|---|
| | n1A | n2A | n1B | n2B | Peeling-off of film | Impact resistance (mA) |
| Ex 11 | 0.02 | 0.06 | 0.00 | 0.01 | I:⊚, O:⊚ | 0 |
| Ex 12 | 0.00 | 0.06 | 0.00 | 0.01 | I:⊚, O:⊚ | 0 |
| Ex 13 | 0.00 | 0.05 | 0.00 | 0.02 | I:⊚, O:⊚ | 0 |

TABLE 3

Formability of resin laminated metallic sheet (3)

| | Orientation coefficient of resin layer | | | | Can properties | |
|---|---|---|---|---|---|---|
| | n1A | n2A | n1B | n2B | Peeling-off of film | Impact resistance (mA) |
| Co Ex 1 | 0.00 | 0.06 | 0.00 | 0.06 | I:⊚, O:Δ | 0 |
| Co Ex 2 | 0.01 | 0.06 | 0.01 | 0.06 | I:○, O:Δ | 0 |
| Co Ex 3 | 0.04 | 0.06 | 0.04 | 0.06 | I:Δ, O:X | 0 |
| Co Ex 4 | 0.01 | 0.07 | 0.01 | 0.07 | I:○, O:X | 0 |
| Co Ex 5 | 0.00 | 0.05 | 0.00 | 0.05 | I:⊚, O:Δ | 0 |
| Co Ex 6 | 0.00 | 0.03 | 0.00 | 0.03 | I:⊚, O:Δ | 0.4 |
| Co Ex 7 | 0.00 | 0.06 | 0.01 | 0.08 | I:⊚, O:X | 0 |
| Co Ex 8 | 0.00 | 0.06 | 0.02 | 0.08 | I:⊚, O:X | 0 |
| Co Ex 9 | 0.02 | 0.06 | 0.04 | 0.08 | I:○, O:X | 0 |

The evaluated results of the thermoplastic resin laminated metallic sheets manufactured using the manufacturing method of a thermoplastic resin laminated metallic sheet of the present invention are shown in Table 1 to 3. Example 1 to 6 are examples wherein biaxially oriented polyester resin films having the same resin composition were laminated on each side of metallic sheets at the various travelling speed of TFS, and those wherein the orientation coefficient n2A of the resin portion at the outermost surface of the resin film laminated on the side to form the inside wall of can body was varied at a fixed travelling speed of TFS. Example 7 to 12 are examples wherein different kind of biaxially oriented polyester resin films were laminated on each side of metallic sheets at the various travelling speed of TFS so that the orientation coefficient of the resin films laminated on the side to form the inside wall of can body were kept constant.

Comparative Example 1 to 6 are examples wherein biaxially oriented polyester resin films having the same resin composition were laminated on each side of metallic sheets at the various travelling speed of TFS using the conventional manufacturing method of a resin laminated metallic sheet, and those wherein the orientation coefficient n2A of the resin portion at the outermost surface of the resin film laminated on the side to form the inside wall of can body was varied at a fixed travelling speed of TFS using the conventional manufacturing method. Comparative Example 7 and 8 are examples wherein different kind of biaxially oriented polyester resin films were laminated on each side of metallic sheets at the various travelling speed of TFS so that the orientation coefficient of the resin films laminated on the side to form the inside wall of can body were kept constant.

The results obtained from these Examples are summarized as follows:

(1) Even when a resin film is laminated on a metallic sheet at high laminating speed, the orientation coefficients (n1A and n1B ) of the resin portions (melting layer) directly contacting the metallic sheet can be controlled within a range of 0 to 0.04 enough for excellent adhesion during forming.

(2) Even when resin films having different resin composition are laminated on a metallic sheet at the various laminating speed, the different orientation coefficient can be obtained on each side of the metallic sheet, and a resin laminated metallic sheet having excellent adhesion during forming and concurrently excellent impact resistance can be obtained.

(3) In a case where the resin films having the same resin composition and the same properties were laminated on each side of a metallic sheet using a conventional manufacturing method, it was impossible to obtain the different orientation coefficient on each side of the metallic sheet, and it is extremely difficult to produce a resin laminated metallic sheet having excellent adhesion during forming and concurrently excellent impact resistance.

(4) In a case where the different kind of resin films (of resin composition or properties) are laminated on each side of a metallic sheet using a conventional manufacturing method, it is possible to obtain the different orientation coefficient on each side of the metallic sheet at a low laminating speed, however, it is extremely difficult to do so at high laminating speed, and it is also too hard to form enough melting layer of the resin layer, resulting in deterioration of the adhesion during forming.

Consequently, it is apparent from the above results that it is possible to always constantly manufacture a thermoplastic resin film laminated metallic sheet having excellent formability, adhesion during forming, and impact resistance at high laminating speed or at various laminating speed using the manufacturing apparatus for thermoplastic plastic resin film laminated metallic sheet and the manufacturing method for thermoplastic resin film laminated metallic sheet of the present invention.

INDUSTRIAL POSSIBILITY IN THE FIELD

Even when the thermoplastic resin film laminated metallic sheet of the present invention is severely formed into can body, the laminated resin films are not peeled off from the inside and outside walls of the produced can body. The thus manufactured can has excellent corrosion resistance to the content packed therein. Besides, by using the manufacturing apparatus and the manufacturing method of the present invention, thermoplastic resin film can be laminated on metallic sheet at high laminating speed, and thermoplastic resin film laminated metallic sheet having stable properties can be produced even when the laminating speed of the resin film is varied. This is a remarkable advantage in the industrial field.

What is claimed is:

1. A manufacturing method for a thermoplastic resin laminated metallic sheet comprising the steps of:

heating a continuously travelling metallic sheet, supplying two thermoplastic resin film having orientation to contact both surfaces of the metallic sheet moving in a traveling direction, pressing the metallic sheet and the thermoplastic resin films using a couple of laminating rolls by pinching them together to laminate them, and thereafter moving a deflector roll, which is disposed downstream from the laminating rolls so as to contact one side thermoplastic resin film laminated on the metallic sheet and movable in a direction at a right angle from the traveling direction of the metallic sheet, to direct the laminated metallic sheet in a direction perpendicular to the traveling direction of the metallic sheet and to a direction opposite to an initial position of the deflector roll, so as to bias the traveling direction of the laminated metallic sheet with thermoplastic resin thereon to wind it round either one of the laminating rolls, wherein the two thermoplastic resin films have different melting temperatures.

2. The manufacturing method for a thermoplastic resin laminated metallic sheet according to claim 1, wherein the orientation coefficient of an outermost layer of one side resin film contacting the deflector roll becomes smaller than that of an outermost layer of the opposite side resin film not contacting the deflector roll.

3. A manufacturing method for a thermoplastic resin laminated metallic sheet comprising the steps of:

heating a continuously traveling metallic sheet, supplying two thermoplastic resin films having orientation to contact both surfaces of the metallic sheet moving in a traveling direction, pressing the metallic sheet and the thermoplastic resin films using a couple of laminating rolls by pinching them together to laminate them, and thereafter moving a deflector roll, which is disposed downstream from the laminating rolls so as to contact one side thermoplastic resin film laminated on the metallic sheet and movable in a direction at a right angle from the traveling direction of metallic sheet, to direct the laminated metallic sheet in a direction perpendicular to the traveling direction of the metallic sheet and to a direction opposite to an initial position of the deflector roll, so as to bias the traveling direction of the laminated metallic sheet with thermoplastic resin thereon to wind it round either one of the laminating rolls, wherein the two resin films have different heat-setting temperatures, respectively, said resin films being prepared by melting thermoplastic resin, elongating and orienting the same in biaxial directions, and therefore thermally setting the same respectively at different temperatures.

4. The manufacturing method for a thermoplastic resin laminated metallic sheet according to claim 3, wherein the orientation coefficient of an outermost layer of one side resin film contacting the deflector roll becomes smaller than that of an outermost layer of the opposite side resin film not contacting the deflector roll.

5. A thermoplastic resin laminated metallic sheet, produced by laminating thermoplastic resin film on metallic sheet, wherein when the orientation coefficient of one surface portion of the thermoplastic resin film contacting the metallic sheet is represented by n1A, the orientation coefficient of the other surface portion of the thermoplastic resin film not contacting the metallic sheet is represented by n2A, said thermoplastic resin film being laminated on one side (A) of the metallic sheet, and the orientation coefficient of one surface portion of a thermoplastic resin film contacting the metallic sheet is represented by n1B, the orientation coefficient of the other surface portion of the thermoplastic resin film not contacting the metallic sheet is represented by n2B, said thermoplastic resin film being laminated on the other side (B) of the metallic sheet, said orientation coefficients are determined within the following ranges:

n1A is 0 to 0.04, n1B is also 0 to 0.04, n2A is 0.02 to 0.10, and n2B is 0 to 0.10, and n1A<n2A, n1B<n2B, n2B<n2A.

6. The thermoplastic resin laminated metallic sheet according to claim 5, wherein said thermoplastic resin is polyethylene terephthalate resin, copolyester resin mainly consisting of ethylene terephthalate recurring unit, polybutylene terephthalate resin, or copolyester resin mainly consisting of butylene terephthalate recurring unit, or blended polyester resin having at least two resins selected from them to blend, or plural-layered laminate polyester resin having at least two resins selected from them.

7. The thermoplastic resin laminated metallic sheet according to claim 5, wherein said thermoplastic resin is a double-layered resin composed of an upper layer and a lower layer, said lower layer being disposed between said upper layer and said metallic sheet, the upper layer including polyethylene terephthalate resin, copolyester resin mainly consisting of ethylene terephthalate recurring unit, polybutylene terephthalate resin, or copolyester resin mainly consisting of butylenes terephthalate recurring unit, or blended polyester resin having at least two resins selected from them to blend, and the lower layer including blended resin to poly carbonate resin and one of the thermoplastic resins forming said upper layer.

8. The thermoplastic resin laminated metallic sheet of claim 5, wherein said thermoplastic resin film laminated on side (A) of said metallic sheet has a different melting temperature from said thermoplastic resin film laminated on side (B) of said metallic sheet.

9. The thermoplastic resin laminated metallic sheet of claim 5 wherein said thermoplastic resin film laminated to side (A) of said metallic sheet has a different heat-setting temperature then that of said thermoplastic resin film laminated to side (B) of said metallic sheet.

* * * * *